United States Patent [19]
Pendergrass, Jr.

[11] Patent Number: 5,565,148
[45] Date of Patent: Oct. 15, 1996

[54] DEVICE FOR SELECTIVELY PROVIDING A MULTIPLICITY OF AROMAS

[75] Inventor: Daniel B. Pendergrass, Jr., Mendota Heights, Minn.

[73] Assignee: Minnesota Mining and Manufacturing Company, St. Paul, Minn.

[21] Appl. No.: 405,040

[22] Filed: Mar. 16, 1995

[51] Int. Cl.⁶ ........................................ B01F 3/04
[52] U.S. Cl. ................... 261/30; 261/DIG. 65; 422/124
[58] Field of Search .............. 261/30, DIG. 65; 422/124

[56] References Cited

U.S. PATENT DOCUMENTS

| | | | |
|---|---|---|---|
| Re. 32,513 | 10/1987 | Seaber et al. | 261/DIG. 65 |
| 3,410,488 | 11/1968 | Sugimura | 261/30 |
| 3,711,023 | 1/1973 | Smith | 261/DIG. 65 |
| 4,157,787 | 6/1979 | Schwartz | 261/DIG. 65 |
| 4,629,604 | 12/1986 | Spector | 422/124 |
| 4,642,945 | 2/1987 | Browning et al. | 52/10 |
| 4,752,065 | 6/1988 | Trumbull et al. | 272/18 |
| 4,771,344 | 9/1988 | Fallacaro et al. | 358/335 |
| 4,790,527 | 12/1988 | Browning | 272/10 |
| 4,826,245 | 5/1989 | Entratter | 297/217 |
| 4,838,344 | 6/1989 | Murakami | 165/48.1 |
| 4,879,849 | 11/1989 | Hollingsworth, III et al. | 52/10 |
| 4,919,197 | 4/1990 | Murakami | 165/48.1 |
| 4,955,945 | 9/1990 | Weick | 261/DIG. 65 |
| 5,023,020 | 6/1991 | Machida et al. | 422/124 |
| 5,026,152 | 6/1991 | Sharkey | 352/85 |
| 5,167,877 | 12/1992 | Pai | 261/DIG. 65 |
| 5,192,247 | 3/1993 | Barr et al. | 472/60 |
| 5,259,062 | 11/1993 | Pelonis | 261/DIG. 65 |
| 5,301,457 | 4/1994 | Seely | 43/132.1 |
| 5,395,047 | 3/1995 | Pendergrass, Jr. | 239/56 |

*Primary Examiner*—Tim R. Miles
*Attorney, Agent, or Firm*—Gary L. Griswold; Walter N. Kirn; James D. Christoff

[57] ABSTRACT

An apparatus for delivering one or more aromas at selected times includes a housing with a receptacle and an aroma delivery device detachably received in the receptacle. The aroma delivery device includes a carrier having a plurality of aroma-bearing elements that are selectively communicated with an air passageway for providing one or more aromas as desired. The device is especially useful for providing a realistic sensory experience in an interactive or non-interactive use, and may be used in such diverse settings as the entertainment industry, the educational training field or a medical arena.

15 Claims, 4 Drawing Sheets

DEVICE FOR SELECTIVELY PROVIDING A MULTIPLICITY OF AROMAS

BACKGROUND OF THE INVENTION

1. Field of the Invention

This invention relates to a device that provides one or more fragrances to a conditioned space and enables the selection of aromas to be easily changed when desired. The device is particularly useful in the fields of education, entertainment and medicine as well as other fields where there is a need for varying the selection of aromas over a period of time.

2. Description of the Related Art

In the fields of education and entertainment, a significant effort has been made to provide simulated experiences that are as realistic as possible. In the education arena, the effort has been most successful in emulators which strive to create the illusion of operating equipment such as aircraft or ships to provide training which would otherwise be too expensive or too dangerous. Early efforts involved the use of detailed models which were moved in response to controls such as, for example, in docking a ship. Later emulations used periscopes and lenses to more accurately recreate the view from the bridge. As computers became available, the controls were modified to provide tactile feedback which better mimicked the degree of effort required to move the controls and thus the "feel" of the helm. As the computational speed of the emulators improved, models that were initially schematic or wire-frame models became more realistic renderings of the surroundings provided on a monitor in front of the student. As the art of building simulators has advanced, the student has been placed in a controlled environment in which the sights, sounds, and attitude which the student experiences within the training module is controlled by computer to provide realistic experiences. More recently, simulation has been used to allow students to explore, "experience" and interact with a variety of environments ranging from the subatomic to the universe itself.

Many of the same interactive display principles have been adapted to the entertainment field in the form of games. Initially those games were little more than computerized boards and playing pieces for conventional games, but those were soon supplemented by role playing adventure games and simulations in which the game environment changed in response to the player's actions and a set of rules, often initially unknown to the player. The earliest of these simulations presented simple text descriptions or tables describing the environment, but soon progressed to simple animated figures moving against stock backgrounds and later to fully rendered foreground and background objects which changed to reflect the positions and actions of the characters.

Parallel developments have also occurred in the presentation of prerecorded materials such as motion pictures. The presentation of some prerecorded material enables the audience to become so involved in the material being presented that it takes on, in some ways, a semblance of reality. The screens used for viewing these works have become larger to encompass more of the visual field and the sound is supplied from multiple sources to provide the sensory illusion of sound sources which move in unison with the visual image. Attempts have been made to present slightly different images independently to the two eyes, usually by means of tinted, prismatic, or polarized glasses to create the appearance of three dimensional objects within the visual space.

As these simulations have improved, the sensory experiences of the student or game player have been manipulated to the point that the viewer becomes sufficiently immersed in the presentation of stimuli that the participant's response is difficult to distinguish from that resulting from exposure to reality. For that reason, the term "Virtual Reality" has been coined to describe a broad range of simulated experiences that are to some extent difficult to distinguish from reality. Some of the current simulations present separate, full-color views of a scene to two small, helmet mounted television screens that fill the visual field to create the illusion of full three dimensional vision. These helmets may optionally be fitted with sensors which detect the movement of the head, or even of the eyes, and allow the computer program creating the images to change the views presented in a dynamic manner. Audio information may also be provided separately and nearly simultaneously to the individual's ears to link a positionally inferred auditory source to an object presented in the visual field.

Two elements which are particularly important to the overall experience are immersion and interaction. With this in mind, it is particularly important to provide stimulation to as many sensory channels as possible and to have all of the stimulation be consistent with the material being presented. Especially in a simple, non-interactive presentation, it is desired to provide consistent stimuli for as many of the five senses as possible in order to maintain the sense of immersion.

SUMMARY OF THE INVENTION

The present invention is directed toward an aroma delivery device wherein a number of aroma-bearing elements are received in separate chambers of a carrier. The carrier is adapted to be releasably received in a receptacle of an apparatus that includes an air passageway that can be selectively communicated with one or more of the chambers when desired. The carrier can be readily removed from the receptacle and replaced with another carrier once the aroma-bearing elements are substantially exhausted, or whenever a different selection of aromas is desired.

More particularly, the present invention in one aspect concerns an aroma delivery device that comprises a carrier having a plurality of separate chambers, and a plurality of aroma-bearing elements each received in a respective one of the chambers. Each of the elements includes a reservoir containing a volatile material and a diffusion rate controlling structure at least partially covering the reservoir. The device also includes at least one cover connected to the carrier for selectively opening one or more of the chambers.

In another aspect, the invention is directed toward an apparatus for delivering a multiplicity of aromas that comprises a housing having an air passageway and a receptacle interposed in the passageway. The apparatus also includes a source of pressurized air for directing air through the passageway, and an aroma delivery device releasably received in the receptacle. The device includes a carrier having a plurality of separate chambers and a plurality of aroma-bearing elements each received in a respective one of the chambers. Each of the elements includes a reservoir containing a volatile material and diffusion rate controlling structure at least partially covering the reservoir. Means is provided for communicating a selected one or more of the chambers with the passageway, and such means includes means for changing the selection of the chambers when desired.

Optionally, the aromas may be provided in a pre-programmed or interactive manner as required by the application. The selection means may be mechanical, an electronic signal embedded in recorded media, an electrical signal generated by an interactive program or a combination of the above. Further, an empty chamber may be provided to assist clearing of the aroma from the conditioned atmosphere or passageways leading to the conditioned atmosphere.

As an example of how the present invention might be utilized in connection with a motion picture or a video game, an aroma-bearing element providing a scent resembling a pizza might be initially provided to the viewer's atmosphere, and then a second aroma-bearing element, scented as appropriate to a pine forest, may be next delivered to the viewer, so that the viewer experiences through the olfactory senses the scenario of carrying a pizza into a pine forest. Other scents, such as aromas resembling flowers or a campfire, might subsequently be provided in accordance with the desired program sequence.

Optionally, the motion picture or video game may be interactive, so that the viewer upon choosing a selected set of actions is then provided with various scents according to an appropriate sequence accompanying the actions. For purposes of illustration, if the viewer in the above example chooses a sequence of actions that results in the pizza being thrown in the campfire, the aroma of fresh pizza could be replaced with an aroma resembling burnt pizza crust and cheese.

The present invention also has utility in the field of medicine. For example, the apparatus of the invention may be used to mask background odors in a surgical suite and provide the benefits of aroma therapy to the surgical team, the patient or both. The apparatus may be used, for instance, with a warming or cooling blanket that supplies conditioned air to an anesthetized patient, and the apparatus may supply a pallet of aromas over a period of time such as a soothing aroma for a pre-operatory setting, another aroma to provide alertness in the operating theater and then a third aroma to suppress nausea during post-operatory recovery.

The detailed description that follows and the accompanying drawings provide further explanation of these and other embodiments of the invention.

DETAILED DESCRIPTION OF THE PREFERRED EMBODIMENTS

Figure 1:
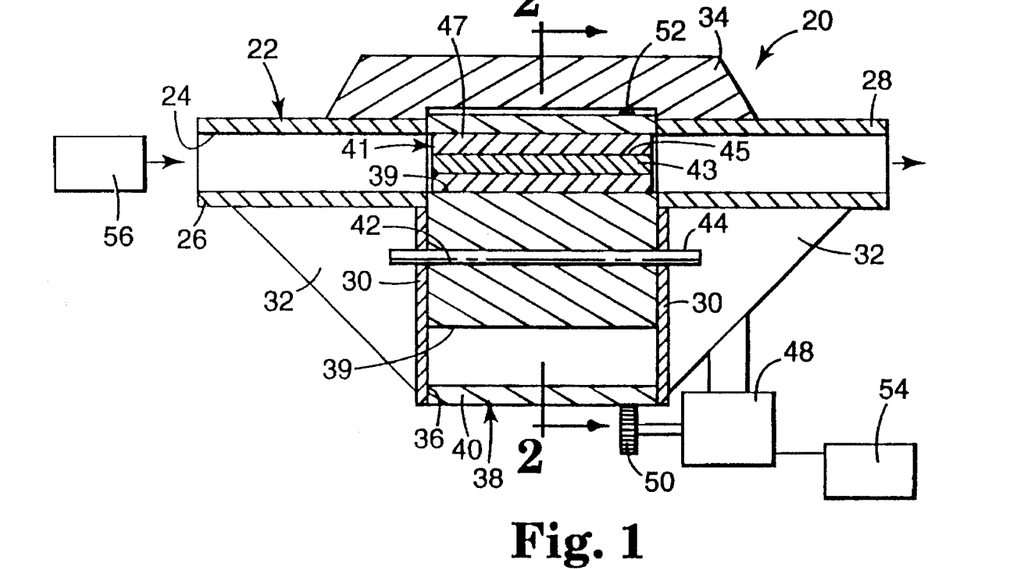
FIG. 1 is a side cross-sectional view of an apparatus for delivering a multiplicity of aromas in accordance with one embodiment of the invention, wherein the apparatus includes a housing and an aroma delivery device releasably received in the housing.

An apparatus for delivering a multiplicity of aromas that is constructed in accordance with one embodiment of the invention is broadly designated by the numeral 20 in FIG. 1. The apparatus 20 includes a rigid housing 22 having an air passageway 24 that enables air to flow through the housing 22 in the direction shown by the arrows in FIG. 1. The air passageway 24 includes a cylindrical air inlet conduit 26 and a cylindrical air outlet conduit 28. The outlet conduit 28 communicates with the space to be fragranced by a passage that preferably is short and does not readily absorb volatile fragrancing materials.

The housing 22 also includes two spaced apart, circular plates 30 that each have an opening fixed to adjacent ends of the air conduits 26, 28. Two reinforcing flanges 32 are also each connected to one of the conduits 26, 28 and the respective, adjacent plate 30. A structural member 34 interconnects the conduits 26, 28, the plates 30 and the flanges 32 and helps to insure that the plates 30 remain fixed at a certain, specified distance apart from each other in parallel relation.

The housing 22 includes a receptacle 36 that is interposed in the passageway 24 between adjacent ends of the conduits 26, 28. An aroma delivery device 38 is releasably received in the receptacle 36 and includes a cylindrical carrier 40 having a bore 42 (see also FIG. 2) extending along its central axis. A shaft 44 (FIG. 1) is detachably received in the bore 42 as well as in two matching, aligned central holes of the plates 30 in order to releasably couple the carrier 40 to the housing 22. A wire spring (not shown) is located next to the outwardly-facing side of each plate 30, and each spring engages an adjacent groove formed on the shaft 44 in order to releasably connect the shaft 44 to the plates 30 and in the position as shown in FIG. 1.

The carrier 40 includes six identically-shaped cylindrical chambers 39 that are parallel to each other and extend from one end of the carrier 40 to the other. The chambers 39 are equally spaced apart from each other and arranged in a circular array in radial fashion relative to a central axis of the carrier 40. In the embodiment shown in the drawings, five of the chambers 39 detachably and slidably receive a respective aroma-bearing element 41, while the sixth chamber 39 is empty.

Each of the aroma-bearing elements 41 includes a reservoir 43, a volatile material received on the reservoir 43 and a diffusion rate-controlling structure 45 that surrounds the reservoir 43. Optionally, and as shown, a layer of lofty material 47 surrounds the structure 45. The elements 41 preferably have a cylindrical shape with a diameter and length that is just slightly smaller than the diameter and length of the chambers 39. Each element 41 is snugly received in the respective chamber 39, and yet can be removed from the latter and easily replaced when desired.

Preferably, each reservoir 43 contains a different volatile material in order to provide different aromas as needed.

A stepmotor 48 is secured to a bracket that is fixed to one of the flanges 32. A gear 50 is connected to the outer end of an output drive shaft of the stepmotor 48 and meshingly engages a row of teeth 52 (FIG. 2) that circumscribe an outer wall of the carrier 40. The stepmotor 48 is electrically connected to a programmable controller 54 that is shown schematically in FIG. 1.

Figure 2:
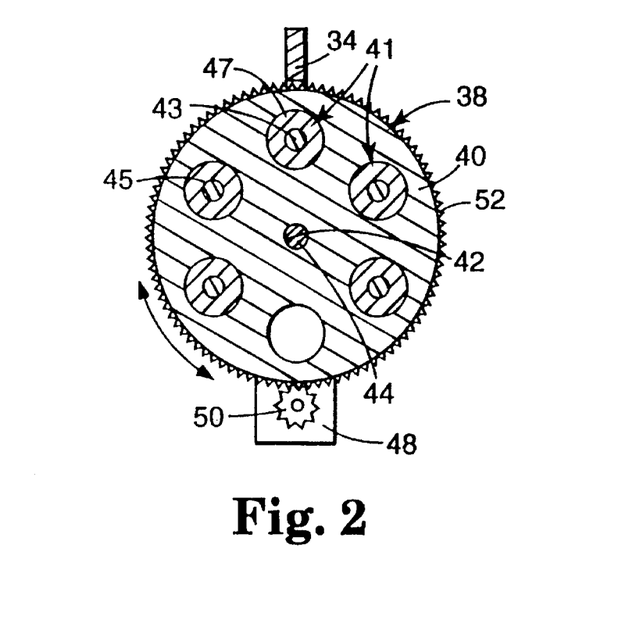
FIG. 2 is an end cross-sectional view of the apparatus of FIG. 1, taken along lines 2—2 of FIG. 1.

The stepmotor 48 is operable to rotate the carrier 40 relative to the housing 22 in an arc about the longitudinal axis of the shaft 44 and consequently in either direction as designated by the double-headed arrow in FIG. 2. The stepmotor 48 moves the carrier 40 in a manner similar to the rotation of a barrel of a multi-shot revolver, and provides a means for communicating a selected one or more of the chambers 39 with the passageway 24. The stepmotor 48 and the controller 54 provide a means for changing the selection of the chambers 39 when desired.

A pressurized air source 56 is also schematically illustrated in FIG. 1 and is connected to the air inlet conduit 26. The pressurized air source 56 could be, for example, a blower, pump or fan, and is selected by determining the intended use of the apparatus 20 (such as, for example, whether the apparatus 20 is intended for use by a single individual within a relatively small conditioned space, or whether the apparatus 20 is instead intended for use in a larger, room-sized conditioned space containing several individuals). Additionally, while the pressurized air source 56 is connected to the inlet conduit 26 as shown in the drawings to provide positive air pressure, it should also be understood that a pressurized air source supplying negative air pressure may also be utilized, and could be instead connected to the outlet conduit 28.

The pressurized air source 56 is also electrically connected to the controller 54. When operating, the pressurized air source 56 directs air through the inlet conduit 26, through the particular aroma-bearing element 41 that resides in the chamber 39 presently aligned with the conduits 26, 28, and subsequently through the outlet conduit 28 and to the environment to be fragranced. The pressurized air source 56 may supply either a steady flow of air through the passageway 24, or alternatively may provide a pulsed flow of air as may be desired to reduce the average flow rate of volatile material to the spaced to be fragranced. Fragranced air passing through the outlet conduit 28 may be discharged directly to the space receiving the aroma, or alternatively may be diluted with another air stream before discharge.

The plates 30 function as a cover to substantially preclude volatile material of the aroma-bearing elements 41 from entering the air passageway 24 when the pressurized air source 56 is operating except for volatile material from the particular aroma-bearing element 41 that is present in the chamber 39 currently aligned with the conduits 26, 28. Optionally, the carrier 40 or the plates 30 carry one or more seals to further inhibit the escape of volatile material from the chambers 39 that are not currently aligned with the conduits 26, 28. For example, the inside, facing surfaces of the plates 30 may be covered with a sheet of resilient material such as an adhesive coated, vapor impermeable film having a resilient foam backing, or alternatively rubber O-ring seals may be embedded in grooves that surround the openings of each chamber 39 on both sides of the carrier 40.

As another option, the structural member 34 may include a telescoping or sliding tongue and groove joint to enable the plates 30 (and respective conduits 26, 28) to move slightly toward or away from each other in straight-line manner when desired. A motive means, such as a pneumatic piston and cylinder assembly, is interconnected with the relatively movable parts of the structural member 34 and is operatively connected through electrical solenoid actuated pneumatic valves to the controller 54. In such an instance, the controller 54 operates the pneumatic valves in such a fashion to enable the piston and cylinder assembly to move the plates 30 slightly away from each other immediately before the carrier 40 is rotated to bring another chamber 39 into alignment with the conduits 26, 28. Once movement of the carrier 40 has been completed, the controller 54 operates the pneumatic valves to cause the piston and cylinder assembly to move the plates 30 toward each other and thereby firmly engage the two ends of the carrier 40 to reduce escape of volatile materials from the chambers 39 that are not currently aligned with the conduits 26, 28.

The chamber 39 that is devoid of an aroma-bearing element 41 is useful to clear the passageway 24 (and optionally clear at least a portion of the conditioned space) of fragrance as may be desired. In FIGS. 1 and 2 the empty chamber 39 is shown at the bottom of the carrier 40. The empty chamber 39 may be selected for use when absence of a fragrance is desired, or when it is desired to at least partially clear the conditioned space of fragrance to avoid fatigue of the olfactory senses.

As another option, an air bypass conduit that is separate from the aroma delivery device 38 may extend from the air inlet conduit 26 to the air outlet conduit 28. In such an instance, electrically actuated valving is provided in the bypass conduit and is operatively connected to the controller 54 for enabling or interrupting the flow of air through the bypass conduit as desired. Additionally, in such an instance all of the chambers 39 may receive an aroma bearing element 41.

The particular selection of the aroma-bearing elements 41 in use, and the sequence of the various selections over a period of time, is provided by the controller 54 and is carried out through operation of the stepmotor 48 as may be required by the application. For example, the controller 54 may be pre-programmed to provide only a certain, pre-arranged sequence of selected aroma-bearing elements 41 as may occur, for example, when a pre-recorded presentation such as is provided by a read-only compact disc player or video cassette player is presented to the user. Alternatively, the controller 54 may be operatively associated with a device that provides an interactive experience such as a training simulator, an arcade game or the like, in which case the selection of aroma-bearing elements 41 as carried out by the controller 54 is determined by the user's responses. The controller 54 provides a means for changing the selection of aromas, and may respond to a mechanical signal, an electronic signal embedded in recorded media, an electronic signal provided by an interactive program or a combination of such signals.

As mentioned above, the pressurized air source 56 may provide either a steady flow of air through the passageway 24, or a pulsed flow of air in instances where the steady flow of air is not desired. The controller 54 is programmed to provide a steady air flow or a pulsed air flow in accordance with the characteristics of the aroma-bearing element 41 that is currently selected and located in the passageway 24. Optionally, the controller 54 may vary the frequency or duration of pulses of air or vary the flow rate of a steady air flow stream in accordance with the currently selected aroma-bearing element 41 in order to at least partially compensate for differences in the sensitivity of the human olfactory system to specific fragrance components. If desired, the apparatus 20 may include sensors that detect identifying means provided on each aroma-bearing element 41 (such as, for example, the type of sensors used in cameras for determining the "DX" rating of the photographic film in current use) so that the controller 54 automatically varies the flow rate of a steady or pulsed flow of air in the passageway 24 in accordance with data stored in the controller 54 concerning the selected aroma-bearing element 41.

Advantageously, the provision of the carrier 40, in combination with the receptacle 36 that releasably receives the carrier 40, enables the aroma-bearing elements 41 to be easily replaced when desired. During replacement, the shaft 44 is removed from the bore 42 and the plates 30, and the carrier 40 is then removed from the receptacle 36. The carrier 40 may be manufactured for single use wherein the aroma-bearing elements 41 are fixed in place in the chambers 39. Alternatively, the carrier 40 may be manufactured for reuse such that each aroma-bearing element 41 is removable from its respective chamber 39 and replaced with new aroma-bearing element when needed.

Although not shown in the drawings, the aroma delivery device 38 is preferably supplied by the manufacturer with a means for covering both end openings of the chambers 39 until such time as the device 38 is placed in the receptacle 36, in order to avoid undue loss of the volatile material from the aroma-bearing elements 41 before use. The cover means may comprise one or more sections of a film that are provided with a pressure sensitive adhesive for removably adhering to the ends of the carrier 40 and substantially preventing escape of volatile materials from the various chambers 39. Alternatively, the cover means may comprise a container having seals that engage both ends of the carrier 40 to prevent undue loss of volatile materials until such time as the carrier 40 is removed from the container.

The volatile material to be delivered by each aroma-bearing element 41 may be any volatile material that is desired to be delivered to a local atmosphere. The volatile material may be of a single volatility, or may be a blend of compounds having different volatilities. Such blended fragrances are said to contain multiple "notes." Preferably, the fragrance blend comprises compounds having similar volatilities to provide a balanced fragrance throughout the fragrance delivery life of the product.

The reservoir 43 is selected from constructions that will hold and deliver volatile material over an appropriate time period desired for delivery of the material. One may, for example, desire to have an aroma-bearing element that will provide very effective short term delivery of fragrance. In such a case, construction of the reservoir 43 may be quite simple and consist only of, for example, a material capable of holding a quantity of volatile material while allowing the material to dissipate over time. Examples of suitable reservoir materials include absorptive sheets, sponges, or pads of fabric capable of accommodating the volatile material. The reservoir material may be a nonwoven or woven fabric, such as a nonwoven polypropylene web. A suitable reservoir material is a nonwoven polymeric mat such as no. P110 oil absorbent pad (from 3M). The reservoir 43 may optionally be an open or closed cell sponge-like material. Alternatively, the reservoir 43 may be a gel material, such as disclosed in U.S. Pat. No. 2,691,615 to Turner. Air may flow either around or through the reservoir 43.

Volatile material may optionally be imbibed in or adsorbed on a solid material of the reservoir 43, either in block or particulate form, that serves as a source of supply of volatile material. Examples of such solid materials are talc, waxes and fatty alcohols, and polymeric particles either having interstices that provide a large amount of surface area to provide sites for adsorbing the flagrance oil on the particle or that are swellable by the fragrance oil. Polymer particles may, for example, be formed in the presence of incompatible materials that are later removed to provide particles having interstices.

Optionally, the volatile material may be initially contained within one or more breakable capsules that are broken by the user only at the time that it is desired to initialize the release of the volatile material. Preferably, the breakable capsules are surrounded by material of the reservoir 43 that will absorb and distribute the volatile material throughout an area having sufficient surface area to facilitate and enhance delivery of the volatile material.

The reservoir 43 preferably is provided with sufficient volatile material that a continuous amount of volatile material is allowed to dissipate from the reservoir 43, but not so much that volatile material flows as a liquid from the device, regardless of the orientation of the device. Thus, the element 41 preferably may be oriented in any position without significant flow of volatile material to the current lower edge of the element 41. Most preferably the element 41 contains volatile material in a sufficiently limited quantity such that one does not release liquid volatile material by squeezing the element 41 with moderate pressure. It is desirable to avoid the possibility of generating liquid volatile material by squeezing because of the potential for misuse, harm or adverse physical reaction to such volatile materials especially when the elements 41 are accessible in a location where children or pets are present.

The diffusion rate-controlling structure 45 enables the volatile material to be delivered in a controlled manner. Most preferably, the volatile materials are delivered in a zero order or approaching a zero order delivery rate. For most effective zero order delivery, the reservoir 43 is capable of delivering the volatile material faster than the diffusion rate controlling aspect of the structure 45.

Preferably, the reservoir 43 provides highly efficient delivery of the volatile material. If the reservoir 43 is highly absorbent, it may not release the volatile material quickly enough to provide rate limitation by the structure 45. Thus, the reservoir 43 preferably has a high surface area that will allow escape of the volatile material in a rapid manner. When the reservoir 43 is a sponge-like structure, preferably it is of an open-cell foam rather than a closed-cell foam. When the reservoir 43 is a non-woven or woven fabric pad, it is preferably prepared from fibers that do not absorb the volatile material. For example, polyethylene fibers are plasticized by fragrance oils, and therefore do not allow diffusion from the pad as readily as other fibers that are not plasticized by the volatile material. Fiber materials such as high density polypropylene and polyester are preferred for controlled delivery devices, because they provide good surface area and texture without absorbing the volatile material. More oleophobic and crystalline fibers are generally preferred. Additionally, these fibers are preferably selected from biodegradable materials.

The diffusion rate controlling structure 45 may be, for example, a membrane such as an essentially continuous film that allows permeation of the volatile material through the film. Alternatively, the structure 45 may be a film imparted with perforations therethrough to allow vapor to be transmitted through the film at a controlled rate. Examples of suitable film material include those made from polyester, polyethylene, polypropylene, polyethylene terephthalate, polyurethane, and the like. These films are provided with perforations to allow controlled escape of the volatile material from the element 41. The size and number of holes provided in the film is determined by the affinity of the volatile material to the reservoir 43 and the volatility of the volatile material. Where multiple notes of a fragrance are to be delivered, each note may be provided in its own section with a different film having a different size and/or number of holes to account for the different volatilities of the notes. Different amounts of components of a fragrance blend may also optionally be provided to adjust for the different volatilities of the flagrance notes. A balanced fragrance may thereby be delivered throughout the flagrance-delivery lifetime of the element 41.

As another alternative, the structure 45 may be a fabric that preferably has a comparatively tight weave for good control of volatile material dissipation. Satin fabrics, for example, may be used. As another option, the structure 45 may be wall surfaces defining a dead air space, such as wall surfaces of the surrounding chamber.

The lofty material 47 surrounding the reservoir 43 is relatively porous and serves as a temporary storage location for air that has been enriched with volatile material exiting the structure 45. Temporary storage of the flagrance-enriched air enables the element 41 to provide rapid response for the delivery of fragranced air to an air flow applied to the selected chamber 39. Suitable lofty material 47 includes a bonded polyester nonwoven style 9230 (1.1 oz. per square yard) from Bonar Fabrics Corporation, Greenville, S.C.

Optionally, the lofty material 47 is surrounded by an open-ended cylindrical shell that is made of, for example, polyester. The shell provides for convenient handling of the aroma-bearing element 41, particularly in those instances where the carrier 40 is intended for reuse and individual elements 41 are removed from their respective chambers 39 and replaced when desired. The shell need not be porous, since air directed through the selected chamber 39 passes through the open ends of the shell.

Figure 3:
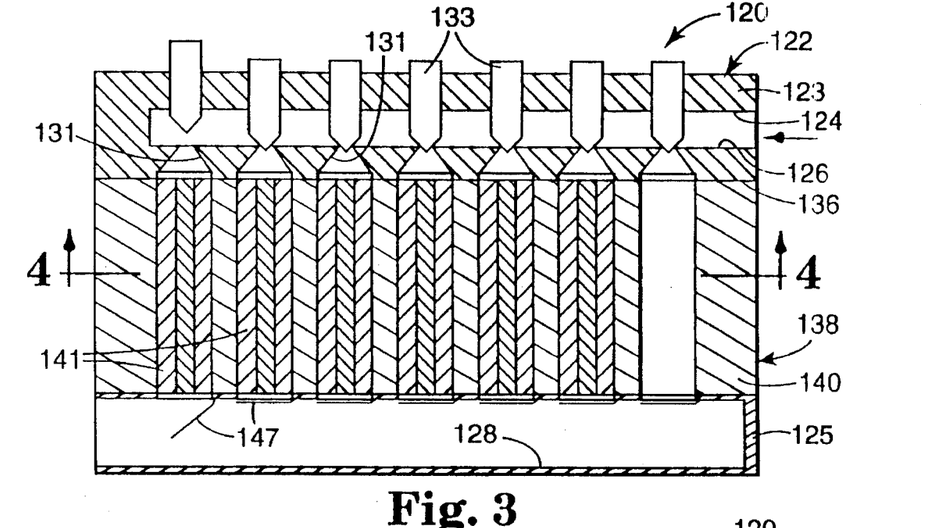
FIG. 3 is a side cross-sectional view of an apparatus for delivering a multiplicity of aromas in accordance with another embodiment of the invention.
Figure 4:
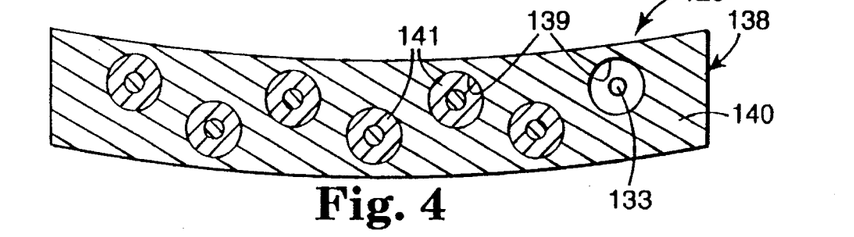
FIG. 4 is a bottom cross-sectional view taken along lines 4—4 of FIG. 3 and showing a number of chambers for receiving aroma-bearing elements.
Figure 5:
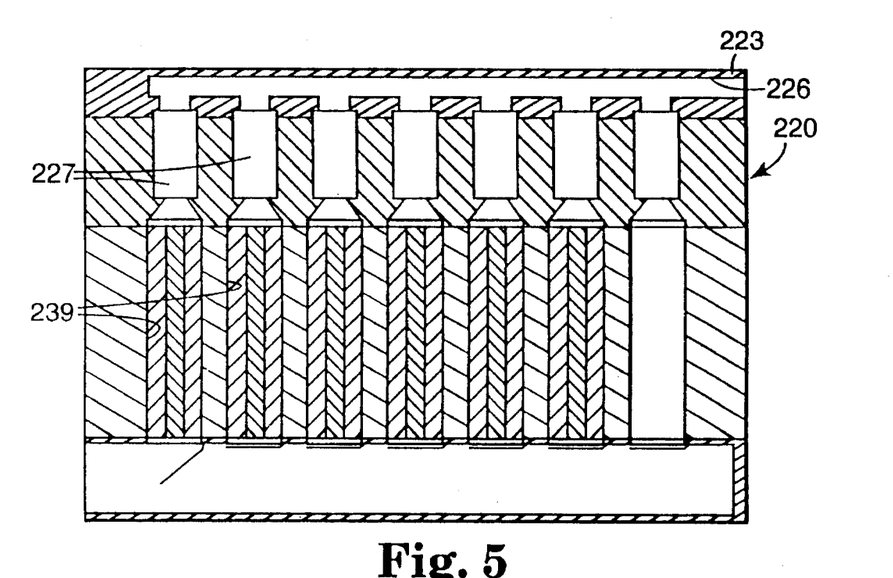
FIG. 5 is a view somewhat similar to FIG. 3 except in accordance with still another embodiment of the invention.

An apparatus 120 according to another embodiment of the invention is illustrated in FIGS. 3 and 4. The apparatus 120 includes a housing 122 that includes an upper portion 123 and a lower portion 125. An air passageway 124 extending through the housing includes an air inlet conduit 126 in the housing upper portion 123 and an air outlet conduit 128 that is located in the lower housing portion 125. The air inlet conduit 126 serves as a manifold that leads to an array of seven ports 131, although a greater or smaller number of ports 131 is, of course, also possible.

The upper housing portion 123 carries seven electrically actuated, solenoid air valves 133 that are shown schematically in FIG. 3. Each air valve 133 is electrically connected to a controller (not shown) that is similar to the controller 54 depicted in FIG. 1. Each air valve 133 includes a valve stem that is movable either toward or away from a position of sealing contact with a respective one of seven openings in the air inlet conduit 126 that each lead to a corresponding port 131.

The space between the upper housing portion 123 and the lower housing portion 125 presents a receptacle 136 for receiving an aroma delivery device 138. A number of bolts (not shown) extend through holes in the housing portions 123, 125 and into threaded openings of the aroma delivery device 138 in order to releasably secure the latter in place in the receptacle 136. As another alternative, a quick-release clamping mechanism or other type of connecting structure can be used to releasably secure the aroma delivery device 138 in the receptacle 136 between the housing portions 123, 125.

The aroma delivery device 138 includes a carrier 140 having seven chambers 139 arranged in a generally linear array. Each chamber 139 is aligned with a respective one of the ports 131 when the carrier 140 is in place in the receptacle 136.

The lower housing portion 125 also has seven openings that are each aligned with a respective chamber 139 when the carrier 140 is in place in the receptacle 136. Each of the seven openings in the lower housing portion 125 is selectively opened or closed by a vapor-impermeable movable cover 147 that is hingeably connected to the lower housing portion 125. In FIG. 3, each cover 147 is integrally joined to the lower housing portion 125 by a living hinge, although other constructions are, of course, possible. Preferably, each cover 147 is resiliently biased by the living hinge or by other structures (such as a spring) toward a closed position so that the chambers 139 that are not currently receiving an incoming pressurized air flow are also not in communication with the air outlet conduit 128.

An aroma-bearing element 141 is received in six of the seven chambers 139. Iach aroma-bearing element 141 is identical to the aroma-bearing elements 41 described in connection with FIGS. 1 and 2, and consequently a detailed description of the elements 14 1 need not be repeated. The chamber 139 that is devoid of an aroma-bearing element is useful as a bypass channel for clearing the conditioned atmosphere or passageways leading to the conditioned atmosphere when needed.

The air valves 133 provide a means for communicating a selected one or more of the chambers 139 with the air passageway 124. The air valves 133 also provide a means for changing the selection of the chambers 139 when desired. When, for example, a certain air valve 133 is opened, the pressure of air passing through the inlet conduit 126 and the respective chamber 139 bears against the corresponding cover 147, enabling the cover 147 to open and pass the flow of air to the outlet conduit 128. Optionally, each cover 147 may be replaced with a solenoid operated air valve similar to the air valves 133.

The apparatus 120 is advantageous in that more than one of the chambers 139 may be in communication with the passageway 124 at any certain selected time. Such construction is useful, for example, in instances where a background aroma (such as the smell of a pine forest) is to be provided to the conditioned space and a second aroma (such as the smell of a pizza) is to be added to the background aroma. The apparatus 120 enables one aroma to be slowly phased in if desired by slightly opening the corresponding air valve 133, while phasing out another aroma by slowing closing the respective air valve 133.

Preferably, the carrier 140 includes one or more seals for avoiding leakage of air or volatile material at locations adjacent the ends of the chambers 139. Such seals could be provided by separate gaskets or O-rings surrounding each open end, or alternatively could be provided by a section of resilient gasket material (such as pressure sensitive adhesive-backed foam tape) that has openings aligned with ends of the chambers 139. As lo such, when the carrier 140 is in place in the receptacle 136, leakage of air or volatile material from the apparatus 120 is diminished.

FIG. 4 illustrates another embodiment of the invention, wherein an apparatus 220 is provided for delivering a multiplicity of aromas. The apparatus 220 is substantially identical to the apparatus 120 except for the differences described in the following paragraphs.

An upper housing portion 223 of the apparatus 220 has an air inlet conduit 226 that is in communication with an inlet end of each of seven air pumps 227. Suitable examples of the air pumps 227 include piezoelectric fans, muffin fans or aquarium fans. In turn, the outlet end of each air pump 227 is in communication with a respective one of seven chambers 239. Each air pump 227 includes an electric motor that is electrically coupled to a controller that is similar to the controller 54 mentioned in connection with FIGS. 1 and 2. As an alternative, the air pumps 227 could be located remotely from the chambers 239 to minimize noise.

Preferably, the air pumps 227 of the apparatus 220 are operable to provide a variable rate continuous flow of air through the respective chamber 239, or a variable rate pulsed flow of air through the respective chamber 239. As such, when a transition from one aroma to another is desired, the flow rates of air from the respective air pumps 227 can be increased or decreased as needed to provide a smooth transition from one fragrance to another. For example, the volume of air from one air pump 227 could be gradually increased per unit time while the volume of air from another air pump 227 could be gradually decreased over the same time interval, in order to introduce a second aroma while depleting the first in the conditioned space.

The variable rate air pumps 227 are also useful to partially compensate for differences in the sensitivity of the human olfactory system to specific fragrance components. For example, a smaller number of pulses per unit time, or a slower motor speed which results in a smaller volume flow rate of air through the respective chamber 239 per unit time, is useful for the presentation of relatively strong aromas. It may also be useful to intermittently decrease the flow rate of air through the selected chambers 239 in order to reduce the likelihood of fatigue of the olfactory senses.

Although not illustrated in the drawings, another embodiment of the invention is directed to an apparatus having a row of parallel chambers that are aligned in a linear array along a central axis of a carrier. All but one chamber receives an aroma-bearing element. The carrier is movable relative to a housing of the apparatus by means of a stepmotor (similar to the stepmotor 48 shown in FIG. 1) having a gear drive that meshes with a row of teeth provided on the carrier. The stepmotor is operable to selectively bring one of the chambers into communication with an air inlet conduit and an air outlet conduit and to change the selection of the chambers when desired.

Figure 6:
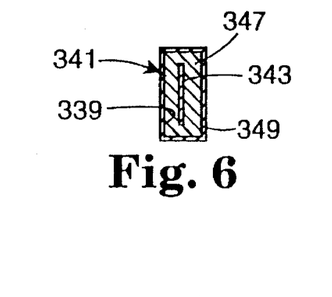
FIG. 6 is a bottom cross-sectional view of a chamber and an aroma-bearing element according to another embodiment of the invention.

FIG. 6 is a cross sectional view of an aroma-bearing element 341 that is complementally received in a chamber 339 according to another embodiment of the invention. The element 341 and the chamber 339 have a rectangular shape, and the element 341 includes a rectangularly-shaped central reservoir 343 that contains a quantity of volatile material. The rectangular shape of the reservoir 343 exposes a relatively large surface area for evaporation of the volatile material in comparison to the reservoir 43 described earlier, and is useful when the rate of volatilization of the volatile material is relatively small. A layer of lofty material 347 surrounds the reservoir 343, and a rectangular polyester shell 349 covers the lofty material 347.

Figure 7:
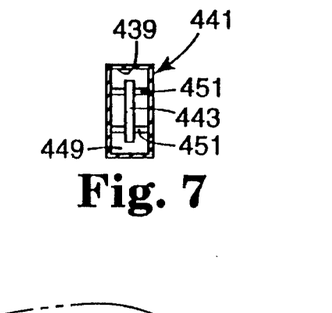
FIG. 7 is a view somewhat similar to FIG. 6 except in accordance with yet another embodiment of the invention.

The aroma-bearing element 44 1 that is depicted in FIG. 7 according to another embodiment of the invention also has a rectangular shape in cross section and is received in a rectangular chamber 439. The element 441 has a reservoir 443 that in this instance comprises a solid material (such as a gel) containing the volatile material. The reservoir 443 is supported by cross bars 451 that are fixed to an inside wall of a surrounding, rectangular shell 449, and no layer of lofty material need be used. Either of the aroma-bearing elements 341, 441 may be substituted for the aroma-bearing elements described in the embodiments above, so long as the respective chambers are of a shape adapted to receive the selected aroma-bearing elements.

Figure 8:
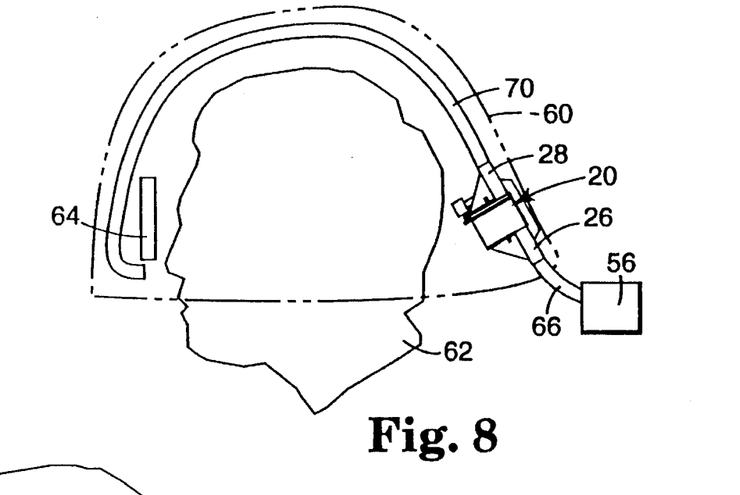
FIG. 8 is a reduced elevational view in partial section of a helmet containing the apparatus illustrated in FIG. 1 for presenting visual and/or audible material along with appropriate, selected aromas.

FIG. 8 is an illustration of a helmet 60 that is worn over the head of an individual 62. The helmet 60 includes one or more screens 64 for presentation of visual material, and optionally includes speakers (not shown) for presentation of accompanying audible material.

The aroma delivery apparatus 20 is connected to a rear portion of the helmet 60, and tubing 66 is provided to communicate the air inlet conduit 26 to the source of pressurized air 56. A second length of tubing 70 is coupled to the outlet conduit 28 of the apparatus 20, and extends inside the helmet 60 to a location directly adjacent the individual's nose for conditioning the relatively small space within the helmet 60 adjacent the nose. A supplemental air flow may optionally be provided for comfort and to facilitate removal of fragranced air to prevent accumulation.

In FIG. 8, apparatus 20 is shown for illustrative purposes. However, the apparatus 120 or 220 could be substituted for the apparatus 20. The apparatus 120 and 220 has a curved overall shape as shown in FIG. 4 to mate with the concave inner surface of the rear portion of the helmet 60. If a large number of aromas are to be provided, more than one of the apparatus 20, 120 or 220 may be employed.

Figure 9:
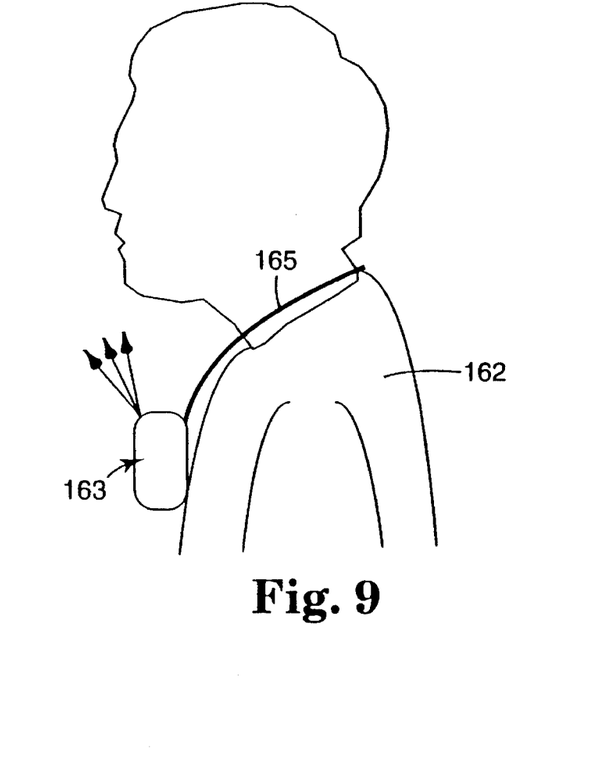
FIG. 9 is an alternative unit for delivering selected aromas to an individual.

In FIG. 9, an individual 162 is wearing a unit 163 that contains an aroma delivery apparatus of the invention, such as apparatus 20, 120 or 220. The unit 163 is connected to a strap 165 that extends around the individual's neck. Air outlet vents are provided to enable selected aromas to be discharged to a conditioned space in the vicinity of the individual's head. The unit 163 as shown in FIG. 9 is especially useful in areas where a projection screen, video monitor or other relatively distant audio or visual source is employed and the atmosphere directly surrounding the viewer is not confined.

Figure 10:
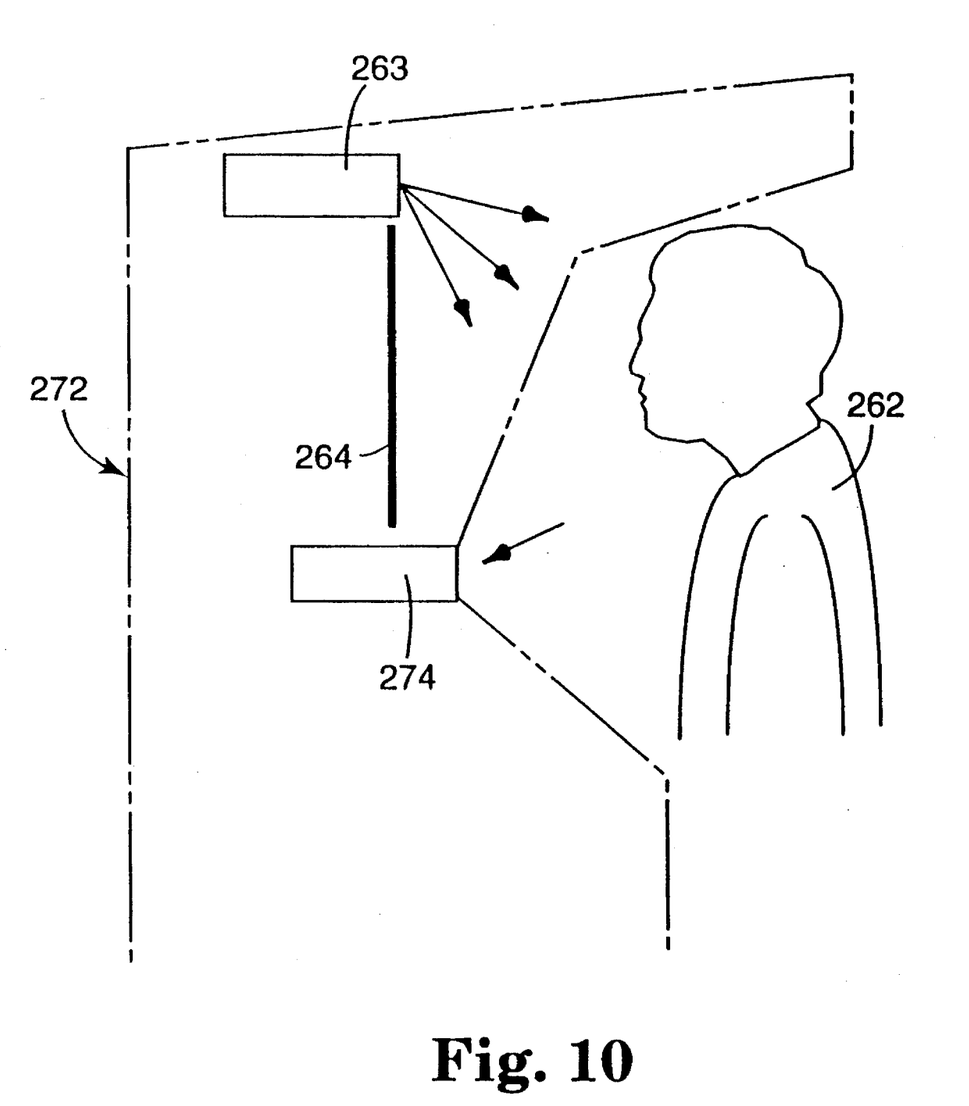
FIG. 10 is a side elevational view of an arcade game wherein a fragranced air flow is directed to a game participant using an apparatus of the present invention.

FIG. 10 illustrates an arcade game 272 wherein a fragranced air flow is directed to an individual 262 participating in the game. The arcade game 272 includes a screen 264 for visual presentations, and preferably also includes speakers for presenting audible material. A unit 263 containing the apparatus 20 delivers a multiplicity of selected aromas to the individual 262, although the apparatus 120 or 220 could be employed as well.

Optionally, an exhaust fan and carbon filter unit 274 is provided to minimize leakage of aroma from the immediate environment of the game. In addition, a curtain may be provided to confine the fragranced air. Local fans may also further control air flow if desired.

I claim:

1. Apparatus for delivering a multiplicity of aromas comprising:

a housing having an air passageway and a receptacle interposed in said passageway;

a source of pressurized air for directing air through said passageway;

an aroma delivery device releasably received in said receptacle, said device including a carrier having a plurality of separate chambers and a plurality of aroma-bearing elements each received in a respective one of said chambers, each of said elements including a reservoir containing a volatile material and diffusion rate-controlling structure at least partially covering said reservoir;

means for communicating a selected one or more of said chambers with said passageway, said means including a controller for changing the selection of said chambers when desired, said device including at least one cover for precluding volatile material from escaping from chambers not in communication with said passageway; and an interactive program, said controller being responsive to electronic signals provided by said interactive program in order to enable the selection of said chambers to be determined by the user's responses to said program.

2. The apparatus of claim 1, wherein said controller is programmable.

3. The apparatus of claim 1, wherein said means for communicating a selected one or more of said chambers with said passageway includes means for moving said carrier relative to said housing, and wherein said carrier has a generally cylindrical shape with a central axis, and wherein said elements are arranged in a circular array about said central axis.

4. The apparatus of claim 1, wherein said means for communicating a selected one or more of said chambers with said passageway includes an air valve.

5. The apparatus of claim 1, wherein said means for communicating a selected one or more of said chambers with said passageway includes an air pump.

6. The apparatus of claim 1, wherein said means for communicating a selected one or more of said chambers with said passageway includes means for moving said carrier relative to said housing.

7. The apparatus of claim 6, wherein said means for moving said carrier relative to said housing includes a stepmotor.

8. The apparatus of claim 1, wherein said means for communicating a selected one or more of said chambers with said passageway includes at least one cover movable relative to said housing.

9. The apparatus of claim 8 and including a stepmotor for incrementally moving said carrier relative to said housing.

10. An aroma delivery device comprising:

a carrier having a plurality of separate chambers;

a plurality of aroma-bearing elements each received in a respective one of said chambers, each of said elements including a reservoir containing a volatile material and diffusion rate-controlling structure at least partially covering said reservoir; and at least one cover connected to said carrier for selectively opening one or more of said chambers, said at least one cover being resiliently biased toward a closed position over one or more of said chambers.

11. The device of claim 10, wherein said elements are arranged in a generally linear array.

12. The device of claim 10, wherein each chamber has an outlet end that is closed by a respective cover.

13. The device of claim 10, wherein said cover comprises a flexible sheet of material and an adhesive for releasably connecting said sheet of material to said carrier.

14. The device of claim 10, wherein said carrier has a central axis, and wherein said chambers are arranged in a circular array about said axis.

15. The device of claim 14, wherein said carrier has a generally cylindrical shape.

\* \* \* \* \*